United States Patent [19]

Fauve

[11] Patent Number: 4,542,212
[45] Date of Patent: Sep. 17, 1985

[54] PHOSPHORYLATED 3-GLYCERYL-ESTERS OF GLUCOSE

[75] Inventor: Robert M. Fauve, Sevres, France

[73] Assignee: Institut Pasteur, Paris, France

[21] Appl. No.: 342,461

[22] Filed: Jan. 25, 1982

Related U.S. Application Data

[63] Continuation of Ser. No. 622,004, Oct. 14, 1975, abandoned.

[51] Int. Cl.$^4$ .............................................. C07H 13/00
[52] U.S. Cl. ..................................................... 536/117
[58] Field of Search ................. 424/180, 198; 536/117

[56] References Cited

FOREIGN PATENT DOCUMENTS 1129M 5/1961 France ................................ 536/117

OTHER PUBLICATIONS

Faldvari et al., "Chem. Abst.", vol. 68, 1968, p. 28,039x.
Nardi et al., "Chem. Abst.", vol. 75, 1971, p. 127696x.
Nojima, "Jour. Biochemistry", vol. 46, 1959, pp. 607–620.

Primary Examiner—Johnnie R. Brown
Attorney, Agent, or Firm—Weiser & Stapler

[57] ABSTRACT

The invention relates to a drug active against infections containing in association with a pharmaceutically acceptable carrier, an active principle which is formed of an ose or a polyose product bearing at least one phosphorylated function and at least one diacylated 3-glyceryl-ester function of formula:

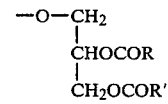

in which the OCOR and —OCOR' groups, which may be the same or different, are derived from fatty acids.

2 Claims, 1 Drawing Figure

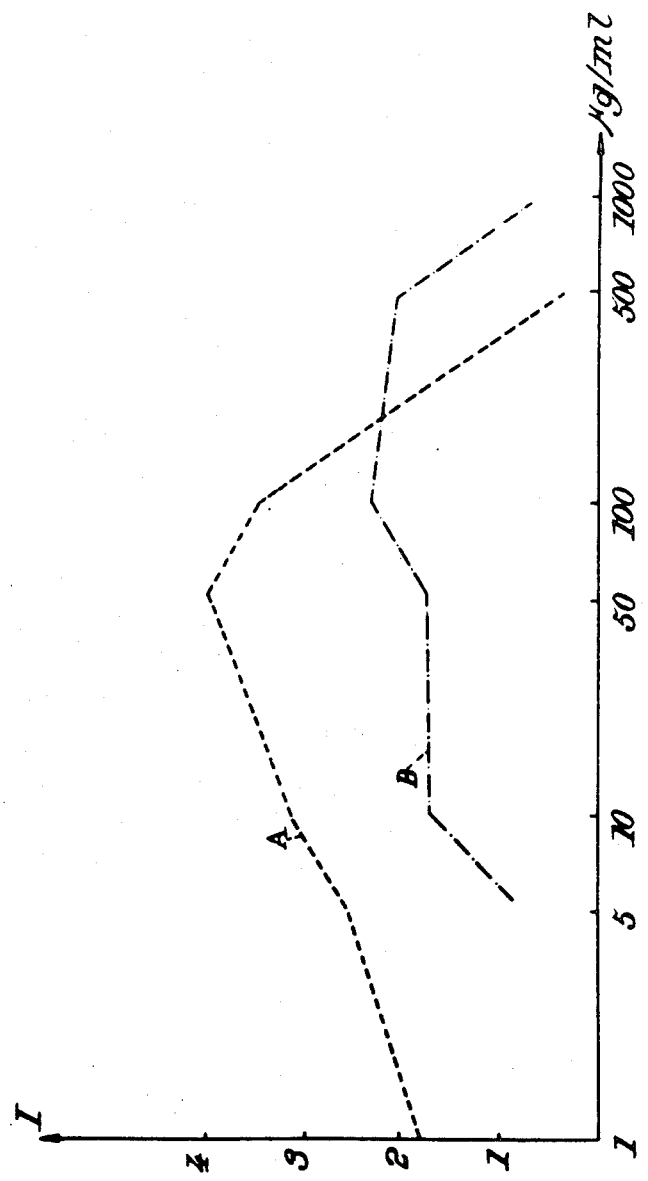

PHOSPHORYLATED 3-GLYCERYL-ESTERS OF GLUCOSE

This is a continuation of application Ser. No. 622,004, filed Oct. 14, 1975, now abandoned.

This invention relates to a drug capable of stimulating non specific resistance of man or animal against external aggressions, especially numerous infectious agents and, in an even more general way, of facilitating or even restoring various organic functions necessary for the biological equilibrium of their organisms.

The drug according to the invention is characterized in that it comprises an active principle consisting of an ose or polyose product bearing at least one phosphorylated function and at least one diacylated 3-glyceryl-ester function of formula:

$$-O-CH_2$$
$$\phantom{-O-}CHOCOR$$
$$\phantom{-O-}CH_2OCOR'$$

wherein the —OCOR and —OCOR' groups are derived from fatty acids, which are either identical or different.

By way of a non-limiting example, the fatty acids under consideration are fatty acids containing from 16 to 18 carbon atoms.

Various phospholipids containing the above defined functions are known. Some of them are available in the trade as laboratory reagents.

In preferred embodiments of the drug of the invention, the phosphorylated function either is part of a glycero-3-phosphoric group of formula:

$$-O-\overset{O}{\underset{\underset{O^-}{\|}}{P}}-O-CH_2$$
$$\phantom{-O-P-O-}CHOH$$
$$\phantom{-O-P-O-}CH_2OH$$

which group is then distinct from the aforesaid diacylated 3-glyceryl-ester function, or forms with the latter a phosphatidyl group of formula:

$$-O-\overset{O}{\underset{\underset{O^-}{\|}}{P}}-O-CH_2$$
$$\phantom{-O-P-O-}CHOCOR$$
$$\phantom{-O-P-O-}CH_2OCOR'$$

in which the —OCOR and —OCOR' groups have the same meanings as above.

Preferably the glycero-3-phosphoric or phosphatidyl groups are linked to one of the ose cycles in said ose or polyose product, either directly or through a methylene group.

The ose or polyose compound is advantageously derived from glucose, mannose or inositol. It may include in its molecule distinct ose groups, for instance both glucose and mannose groups.

Advantageously the ose or polyose product of the kind aforesaid includes several phophoryl functions.

Representative members of active principles according to the invention are the following:

phosphatidylinositol, diphosphoinositide, triphosphoinositide, having respectively the following formulae:

Among the particularly active products one cites:

1. the phosphatidylinositol mannosides of formula:

'n which the —OCOR and —OCOR' groups have the same meanings as above, the group "Man" stands for mannose and x is an integer of 1, 2, 3 or 4;

2. the diglucoside derivative bearing glycerophosphoric functions of either of the following formulae:

-continued

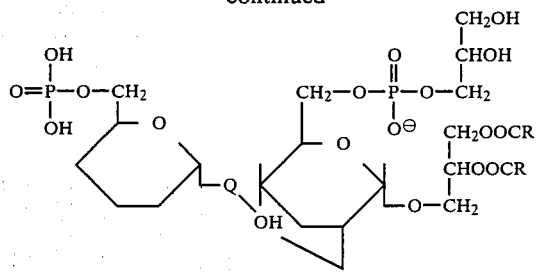

in which the free ol groups of glycerophoshoric functions in said diglucosides may also be acylated by fatty acids.

3. the glucosaminyl-phosphatidyl-glycerols of formula:

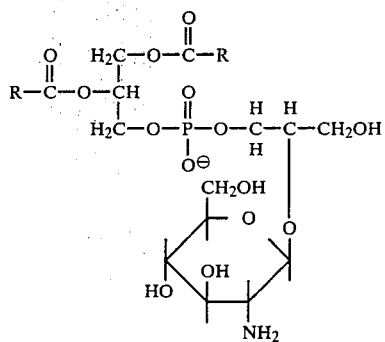

in which R has the above indicated meaning.

The pharmacological tests which will be described later have been effected by using, as active compounds, phosphatidylinositol, diphosphoinositide, triphosphoinositide, phosphatidylinositol mannoside and the diglucoside derivative, the formulas of which have been disclosed before. Phosphatidylinositol, diphosphoinositide and triphosphoinositide are commercially available. They may also be prepared by the method described by B. J. Holub, A. Kuksis, and W. Thomson, J. Lipid. Res., 1970. Vol. 11, p. 558. Phosphatidyl-inositol mannoside has been prepared according to the method described by J. Asselinear Biochem. Biophys. Acta, 1961. Vol. 54, p. 359.

The diglucoside derivative has been obtained as follows:

A bacterial suspension has been prepared in a mixture of solvents formed of a halogenated hydrocarbon, in particular chloroform, and an alcohol, especially methanol; the insoluble fractions have been thereafter separated e.g. by centrifugation, the liquid fraction has been collected and evaporated, under reduced pressure and at a reduced temperature; the solid residue was taken up in chloroform and the chloroform solution was recovered by filtration. The diglucoside derivative of the invention can be obtained from such a solution.

This diglucoside derivative can also be obtained from bacteria both pathogenic (*Vibrio cholera, Mycobacterium tuberculosis, Listeria monocytogenes, Salmonella typhimurium*) and non pathogenic bacteria (*Escherichia Coli* K 12, *Coryne bacterium parvum*), from gram-positive (*Listeria monocytogenes*) or gram-negative bacteria (*Salmonella typhimurium, Escherichia Coli* K 12, *Mycobacterium tuberculosis*) or from anaerobic bacteria (*Coryne bacterium parvum*). It can also be obtained from *Bacillus subtilis, Enterobacter liquefaciens parahaemolytic Vibrio*, etc. . . . .

By way of example it has been obtained by resorting to the following operational sequence applied to bacteria *Salmonella typhimurium* (strain C5 of Institut Pasteur collection).

10 volumes of a mixture consisting of equal volumes of chloroform and methanol, were added to *Salmonella typhimurium* cells at the rate of 10 volumes of this mixture for one volume of said cells.

The obtained mixture was homogenized by means of a crusher during 2 hours at $+4°$ C. and then centrifuged at 3500 G during 20 minutes. The supernatant was introduced in a flask and evaporated under vacuum (water siphon) at a temperature of 40° C. The flask was then fitted with an amount of chloroform having a volume double that of the original sample and was then rotated at 40 RPM during 30 minutes. Thereafter the chloroform solution was filtered on Whatman paper No. 3. The obtained solution (referred to thereafter as "total extract") was adjusted with chloroform so as to obtain a solution containing 100 mg dry weight/ml of the immunostimulant agent. A 0.5 ml portion of the latter solution was deposited onto a length of 5 cm in the lower part of a chromatography plate of silica gel (2 mm thickness). The plate was then introduced into a chromatography vessel such that the portion of the plate bearing said solution was partially immersed in a fractionating mixture consisting of 25 parts of methanol, 65 parts of chloroform and 4 parts of water (parts in volume). Exposure of the plate, respectively to U.V. rays, iodine vapors and ninhydrine aerosol brought into evidence eight clearly distinct spots or fractions, numbered hereafter I to VIII, spot I corresponding to the fraction which migrated to the remotest position and spot VIII to the fraction which migrated the least from the position of the initial deposit.

More specifically the spots were brought to evidence as follows:

Four hours after introduction of the plate into the chromatography vessel, it was exposed to U.V. rays, which permitted the detection of fractions capable of being colored by U.V. rays.

After drying at 37° C. in an air oven, the plate was exposed to iodine vapors.

The plate was thereafter maintained in the air oven at 37° C. for a time sufficient to permit elimination of the iodine and then subjected to a ninhydrine aerosol and exposed during 10 minutes at 100° C., whereby the fractions colorable by ninhydrine became detectable.

Spots III, IV, V, VII and VIII were detectable by U.V. rays.

Spots I, II, V, VI, VII and VIII were detectable by iodine vapors.

Spots V, VII and VIII were colored by ninhydrine.

The fractions so characterized were scraped and recovered from the plate of silica gel. They were eluted with the afore said methanol/chloroform/water mixture, to yield the following respective fractions (corresponding to spots I to VIII):

I: 117 μg
II: 73 μg
III: 154 μg
IV: 154 μg
V: 517 μg
VI: 87 μg
VII: 51 μg
VIII: 312 μg

Fraction VI (which is detectable by vapors of iodine only) and which contains the above identified diglucoside as a main component, was found to contains most of the immunostimulant activity of the total extract as was shown by the following experimental results.

Each of these fractions was administered to 10 mice. Accordingly each of these mice received one tenth of the doses indicated hereabove by the intravenous route. By way of comparison 10 other mice were respectively injected with 100 µg of the "total extract" by the intravenous route and 10 others received physiological serum only.

Eighteen hours later, all mice were infected by the intravenous route with $7.5 \times 10^6$ bacteria of the *Salmonella typhimurium* C5 strain. Two hours later, samples of blood were taken from the different mice and a bacterial count was effected on each of the blood sample. The results (expressed as the number of germs per ml of blood) were as follows:

Mice treated with 100 µg of the total extract—$2 \times 10^4$
Mice treated with 0.5 ml of physiological serum—$1.5 \times 10^6$
Mice treated with 11.7 µg of Fraction I—$2.7 \times 10^6$
Mice treated with 7.3 µg of Fraction II—$6.4 \times 10^5$
Mice treated with 15.4 µg of Fraction III+I-V—$1.1 \times 10^6$
Mice treated with 51.7 µg of Fraction V—$6.5 \times 10^5$
Mice treated with 8.7 µg of Fraction VI—$4 \times 10^4$
Mice treated with 5.1 µg of Fraction VIII—$1.1 \times 10^6$
Mice treated with 31.2 µg of Fraction VIII—$1.9 \times 10^6$ The preceding results bring into evidence the significant action of Fraction VI with respect to the proliferation of *Salmonella typhimurium*.

In another series of tests Fraction VI was found to exert substantially the same effect than a 10 times greater dose of the total extract, when injected in mice infested 18 hours thereafter with *Listeria monocytogenes*.

The active principle according to the invention may then also be considered as being essentially formed of a phospholipid identifiable by the fact that it is detectable by iodine but detectable neither by U.V. rays nor by ninhydrine.

More particularly, it may then also be defined as being formed of a phospholipidic fraction, isolatable from bacteria, which is characterized in that a chloroformic solution thereof deposited on a chromatography plate of silica gel yields substantially a single migration spot which is detectable by iodine, but identifiable neither by U.V. rays nor by ninhydrine, when the part of said plate which carries said deposit has been partially immerged in a fractionating medium formed of a mixture of 25 parts of methanol, 65 parts of chlorform and 4 parts of water (parts in volume).

It can also be defined as a phospholipid which has the structure of that which is obtained by chromatographic fractionation of a chloroformic solution which is obtained by a method which comprises essentially forming a suspension of bacteria, such as of the *Salmonella typhimurium* strain, in a mixture of a halogenated hydrocarbon, such as chloroform, and of an alcohol, such as methanol, preferably crushing said bacteria within said solvent mixture, removing the solid fraction and recovering the liquid fraction, evaporating the latter under reduced temperature, preferably lower than 60° C., if need be under reduced pressure, taking up the solid residue in chloroform, removing the solids, whereby the above said chloroformic solution is obtained, the phospholipid having said above structure being that which is contained in the chromatographic fraction obtainable from said chloroformic solution, which is detectable by iodine, but identifiable neither by U.V. rays nor by ninhydrine.

It is also possible to obtain an extract containing the above diglucoside derivative from above defined chloroform solution, by contacting this chloroform solution with acetone and recovering the precipitate containing said diglucoside derivative. If required, the precipitate is taken up again in chloroform and the new chloroform solution so obtained is again contacted with acetone, the final precipitate having a relatively higher content of diglucoside derivative.

An extract of this type called thereafter "acetonic extract" was obtained under the following operational conditions from the chloroform solution containing the "total extract" obtained from *Salmonella typhimurium*.

10 volumes of acetone were added to that chloroformic solution. The formed precipitate was taken up in chloroform until complete dissolution and acetone was added again to the solution so obtained, in a proportion of 10 volumes acetone per volume of chloroform solution. The precipitate obtained was placed thereafter in a nitrogen stream until complete removal of acetone. The obtained precipitate constitue the aforesaid "acetonic extract".

This precipitate was again brought into solution in chloroform, the solution was thereafter contacted with an injectable liquid solution, in particular a sodium chloride physiological solution, while an inert gas, such as nitrogen, was bubbled in the mixture until complete removal of the chloroform. The obtained suspension was homogenized in order to reduce the size of the solid corpuscles until said suspension no longer contained any particles having a diameter substantially larger than 0.5 micron (as checked with microscope and phase contrast). The acetonic extract was used in this form in the pharmacological tests described hereafter.

The other tested compounds were used under the same form too.

(1°) Protection of mice against infections caused by *Listeria monocytogenes*

The active principles of the drugs of the invention protect mice against infections caused by *Listeria monocytotenes*. This test makes use of the fact that Listeria can only develop in the macrophages of liver and spleen of the mouse. Products to be tested which are identified in the left col. of table I thereafter, have been administered as suspensions of sufficiently fine particles to enable them to be injected intravenously at a dosage of 500 micrograms per mouse. 15 hours later, the mice received an i.v. injection of a suspension of *Listeria monocytogenes* bacteria at the rate of $5 \times 10^4$ bacteria per mouse. 48 hours after infection all animals were sacrificed by cervical sectioning; the livers and the spleens were removed, crushed and, after dilution, seeded on agar. Bacterial counts effected on these culture permitted the determination of the number of living Listeria contained in the spleens and the livers of treated mice 8 hours after infection.

The obtained results were compared to those obtained in control mice which had been infected but did then receive physiological serum only.

TABLE I

| Tested products, injection of 500 μg i.v., 15 hours before infection with $5 \times 10^4$ Listeria | Nr. of bacteria found in spleen and liver of mice 48 h. after injection (average for 5 mice p. group). | |
|---|---|---|
| | spleen | Liver |
| (1) 0.5 ml physiological serum | $2.3 \times 10^7$ | $1.2 \times 10^7$ |
| (2) acetonic extract | $2 \times 10^5$ | $4.2 \times 10^4$ |
| (3) phosphatidylinositol | $2.5 \times 10^6$ | $8.2 \times 10^5$ |
| (4) diphosphoinositide | $8.1 \times 10^5$ | $5.2 \times 10^5$ |
| (5) triphosphoinositide | $3.4 \times 10^5$ | $7.4 \times 10^4$ |
| (6) phosphatidyl inositol mannoside | $4.2 \times 10^5$ | $2.4 \times 10^4$ |
| (7) diphosphatidylglycerol | $10^7$ | $6.3 \times 10^6$ |
| (8) lysocardiolipine | $1.8 \times 10^7$ | $1.1 \times 10^7$ |
| (9) phosphatidylcholine | $8 \times 10^6$ | $8.6 \times 10^6$ |
| (10) phosphatidylethanolamine | $6.5 \times 10^6$ | $7.1 \times 10^6$ |
| (11) glycerylphosphorylcholine | $6.7 \times 10^6$ | $6.4 \times 10^6$ |
| (12) phosphatidylserine | $1.5 \times 10^7$ | $8.9 \times 10^6$ |
| (13) cephaline | $7.4 \times 10^6$ | $8.2 \times 10^6$ |
| (14) sphingomycline | $8.4 \times 10^6$ | $1.1 \times 10^7$ |

This table shows that 48 hours after infection, the number of bacteria found in the spleens and livers of control mice had considerably increased. On the contrary, in those which received products 2 to 6, the number of Listeria had practically not increased. It had even decreased substantially in the mice which had received the most active products. The drugs of the invention thus considerably improve the bactericidal action of macrophages, especially macrophages of the spleen and of the liver. Product 7 to 14 have been used for purpose of comparison and have proved to be substantially inactive.

(2°) Elimination from blood of *Salmonella Typhimurium*

The agents of the invention accelerate the elimination of Salmonella from blood. Mice having received 500 μg of the products under study in the same conditions as in the preceding test were given 16 hours later $8 \times 10^6$ Salmonella by i.v. injection. 2 hours after infection, mice were anesthetized with ether. Blood samples were taken from their auxiliary arteries and, after dilution, were seeded on nutrient agar. It was thus possible to determine the number of bacteria which were present in the blood of animals 2 hours after infection.

Results are shown in table II hereunder. The same test has been carried out on control animals (control group) which had received, prior to the infection, only 0.5 ml of physiological serum by i.v. injection. Results obtained with animals treated with trioleine, used for purpose of comparison, are also shown. Each group comprised 3 mice. The values shown in table II are those measured on each mouse and in each group.

TABLE II

| Control group (physiological serum) | 3.2<br>4.1 $\times 10^6$<br>4.5 |
|---|---|
| trioleine group | 1.4<br>2.1 $\times 10^6$<br>2.3 |
| phosphatidyl-inositol group | 1.2<br>1.4 $\times 10^5$<br>2.4 |
| diphosphoinositide group | 1.2<br>0.8 $\times 10^5$<br>0.7 |
| triphosphoinositide group | 4<br>5.8 $\times 10^4$<br>6.4 |

This test brings clearly into evidence the fact that the active principles of the invention induce a substantial acceleration of the elimination of infectious bacteria.

The foregoing results also illustrate the fact that the phospholipids which do not include an ose or polyose portion are not active. Moreover, a triglyceride having no phosphoryl group or no ose group does not provide a measurable activity. The foregoing test further establishes a correlation between the number of phosphoryl groups and the biological activity of the compounds of the invention. The larger the number of phosphate groups, the greater the activity.

(3°) Action of derivatives of the diglucoside type on blastic in vitro conversion of lymphocytes in the spleen of the mouse Mouse spleens, which had been previously recovered, were dissociated in Hanks' liquid and the obtained cellular suspension was filtered on a sieve having 60 microns mesh size. 0.5 ml of a cellular suspension in medium 199 containing between $0.5 \times 10^6$ and $10^7$ cells, 0.05 ml of human serum and 0.05 ml of a suspension of diglucoside in water were introduced into microtubes adapted for tissue cultures. Various tests were effected with increasing concentrations of diglucoside, as from 1 to 100 μg/ml.

42 hours later, 0.05 ml of a solution containing tritiated thymidine was added at the rate of 10 microcuries/ml., 4 hours later, the tubes were centrifuged at 1 500 G during 10 minutes. The centrifugation residue was resuspended in 0.5 ml of physiological serum.

0.5 ml of 10% chloroacetic acid were added to the suspension. The precipitate was recovered on a Whatman GS/C filter under partial vacuum (60 cm water). The filter and the tube were rinsed with 5% trichloroacetic acid and 1 ml of 90° ethyl alcohol. After drying the precipitates on the corresponding filters, the latter were introduced into flasks suitable for scintillation counting. The counting was effected in a liquid-scintillation counter. The counts provided the mitotic indexes which consist of the ratios of the number of observed disintegrations in the cultures in the presence of the diglucoside derivative to the numbers of disintegrations observed in control cultures.

The curves represented on FIG. 1 show the variations of the mitotic indexes (I) as a function of the concentration—in μg/ml—of diglucoside (curve A) and by way of comparison of the "total extract" (curve B).

This figure shows the substantial activity of the diglucoside in concentrations between 1 and 100 μg/ml, whereas a substantial action of the "total extract" is denoted only starting with a dose of 10 μg/ml (active between 10 and 500 μg/ml).

(4°) Other biological activities of the active principle of the drug according to the invention Paludism: It has been found that when mice receive 2 500 sporozoites and 24 hours later 250 μg of acetonic extract, all control mice exhibit parasited hematia 8 to 30 days later, whereas, during the same period, neither of the treated mice bears any parasits.

Cicatrizing activity: Sores having 8 mm diameter have been formed on the skin of mice. 2 hours later mice received 1 mg of acetonic extract by i.v. or subcutaneous injection, or topically. 7 days later, the sores of the treated mice were healed and epithelialized whereas those of the control mice were not.

Pharmacological adjuvent: The injection of 500 μg of acetonic extract to mice enables the dosage of barbiturics necessary for anesthesia to be reduced by half.

Psychotropic action: when mice were treated by the acetonic extract (1 mg) by i.v. route and were placed in the same cage as control mice, the latter reacted less to sound stimulation and the spontaneous activity thereof was smaller than that of the treated mice.

Hypolipemic action: when mice receive the acetonic extract by i.v. route, the chylomirons which appear in blood after their ingestion through gastric probe of 0.5 ml of olive oil are eliminated much quicker.

The agents according to the invention can thus form the active principles of the indicated drugs which can be used, in particular for the curative prophylactic treatment in man and animals of infectious diseases caused by bacteria or virus, e.g. infections of the type caused by tuberculosis, pasteurellosis, brucellosis, listeriosis or infections by gram-negative bacterias. They may also be used for the treatment of diseases due to parasites which, in the course of a phase of their development cycle pass into the blood or lymphatic system, as for example those which are responsible for paludism, bilharziosis or filariosis. They can also be used for treating toxic infections. Owing to the speed of their action, the agents of the invention may be used for preventing post-surgery infections of all types. They may also be used for the preparation of cicatrizing drugs.

They can be administered by intravenous, intramuscular or sub-cutaneous routes, when suspended in pharmaceutically acceptable and sterile liquids, such as solutions of physiological serum (saline solution or glucosed serum) at unit dosages which range from about 0.05 to about 10 mg and, in particular, from 0.1 to 5 mg. In the suspensions the particles of active products must obviously have sizes compatible with injection, i.e. below 10 microns and preferably below 0.5 micron.

They can also be incorporated into a gel suitable for administration by intradermal, sub-cutaneous or intramuscular route, such as a gel of calcium phosphate.

Hereunder is given one example of preparation of a gel containing an active agent in accordance with the invention and suitable for administration by the enumerated routes.

To 40 ml. of a suspension of physiological serum containing the active agent at the desired concentration, is added 5 ml of a solution of anhydrous sodium phosphate PO$_4$HNa$_2$ containing 7.92 g. of sodium phosphate per 100 ml, and 5 ml of a calcium chloride solution containing 8 g. of anhydrous calcium chloride per 100 ml.

The obtained precipitate is centrifuged and taken up in apyrogenous physiological serum in order to obtain the desired concentration of the active agent.

The active agents of the invention can also be administered orally, if associated to solid or liquid pharmaceutically-acceptable excipients. They can also be administered by the rectal route, provided the products are associated with excipients suitable for that kind of administration. They can also be administered externally, e.g. in the form of an aerosol including a suitable vehicle, for example for the treatment of nose infections.

The agents according to the invention can also be used as active principles in ointments, in particular in the treatment of external cicatrization. The ointments can be prepared by any means known per se, using pharmaceutical excipients of conventional type, for ex. lanoline. The concentration of the active principle in such an ointment is normally between 0.5 and 2% by weight.

We claim:

1. A phospholipid compound, isolatable from bacteria, which is a glucose bearing a phosphoric acid group and at least one diacylated 3-glyceryl-ester group of the formula:

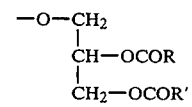

wherein the —OCOR and —OCOR' groups, which may be the same or different, are fatty acids of 16-18 carbon atoms.

2. The phospholipid of claim 1 which is a diglucoside selected from the group having the formulae:

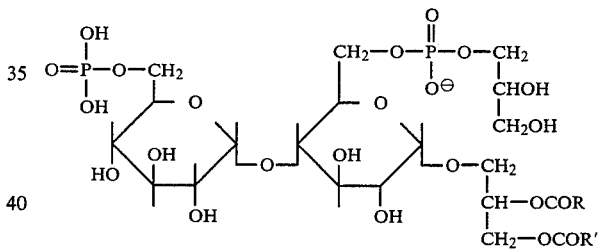

or

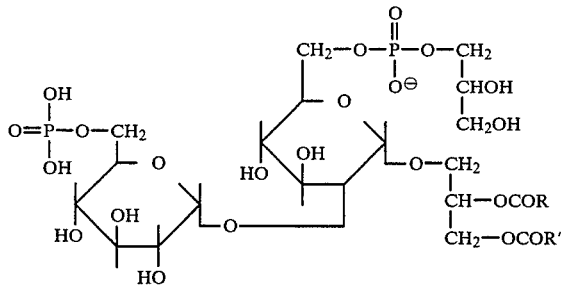

and wherein —OCOR and —OCOR' are as defined in claim 1.

* * * * *